(12) United States Patent
Prinz et al.

(10) Patent No.: US 9,068,002 B2
(45) Date of Patent: Jun. 30, 2015

(54) TREATMENT OF MULTIPLE SCLEROSIS AND/OR RHEUMATOID ARTHRITIS

(75) Inventors: Marco Prinz, Freiburg (DE); Wolfgang Bruck, Rosdorf (DE); Alexander Mildner, Hemmingen (DE); Matthias Mack, Regensburg (DE)

(73) Assignees: GEORG-AUGUST-UNIVERSITAT GOTTINGEN STIFTUNG OFFENTLICHEN RECHTS, Gottingen (DE); UNIVERSITAT REGENSBURG, Regensburg (DE)

( * ) Notice: Subject to any disclaimer, the term of this patent is extended or adjusted under 35 U.S.C. 154(b) by 343 days.

(21) Appl. No.: 12/295,718

(22) PCT Filed: Apr. 2, 2007

(86) PCT No.: PCT/EP2007/002929
§ 371 (c)(1),
(2), (4) Date: Feb. 5, 2009

(87) PCT Pub. No.: WO2007/115713
PCT Pub. Date: Oct. 18, 2007

(65) Prior Publication Data
US 2009/0311273 A1 Dec. 17, 2009

(30) Foreign Application Priority Data
Apr. 3, 2006 (DE) .......... 10 2006 015 341

(51) Int. Cl.
*C07K 16/28* (2006.01)
*A61K 39/395* (2006.01)
*A61K 39/00* (2006.01)

(52) U.S. Cl.
CPC ....... *C07K 16/2866* (2013.01); *A61K 2039/505* (2013.01)

(58) Field of Classification Search
CPC ........... C07K 16/2866; C07K 2316/96; C07K 2317/76; A61K 2039/505
See application file for complete search history.

(56) References Cited

U.S. PATENT DOCUMENTS

| | | | |
|---|---|---|---|
| 5,530,101 A * | 6/1996 | Queen et al. ............... | 530/387.3 |
| 6,084,075 A * | 7/2000 | Lind et al. ................. | 530/388.22 |
| 6,312,689 B1 * | 11/2001 | LaRosa ....................... | 424/130.1 |
| 6,696,550 B2 * | 2/2004 | LaRosa et al. ............. | 530/388.23 |
| 6,723,538 B2 * | 4/2004 | Mack et al. ................. | 435/69.7 |
| 2003/0148963 A1 | 8/2003 | Tarkowski et al. | |
| 2004/0151721 A1 | 8/2004 | O'Keefe et al. | |
| 2005/0048052 A1 | 3/2005 | LaRosa | |

FOREIGN PATENT DOCUMENTS

| | | |
|---|---|---|
| DE | 69727382 | 11/2004 |
| EP | 0914345 | 5/1999 |
| WO | WO-97/31949 | 9/1997 |
| WO | WO 97/31949 A | 9/1997 |
| WO | WO-00/05265 | 2/2000 |
| WO | WO 00/05265 A | 2/2000 |
| WO | WO-01/57226 | 8/2001 |
| WO | WO 01/57226 A | 8/2001 |
| WO | WO 2005/060368 | 7/2005 |
| WO | WO-2005/060368 | 7/2005 |

OTHER PUBLICATIONS

Witte et al, Cancer and Metastasis Reviews 17: 155-161, 1998.*
Stancoviski et al, Proceedings of the National Academy of Science USA 88: 8691-8695, 1991.*
Riemer et al, Mol. Immunol. 42:1121-1124, 2005.*
Vergunst et al., Arthritis & Rheumatism 58(7): 1931-1939, Jul. 2008.*
Xia et al., Expert Opinion 19(3): 295-303, 2009.*
Wagner, Dissertation 2001.
Biber, Knut et al., "Expression of L-CCR in HEK 293 cells reveals functional responses to CCL2, CCL5, CCL7, and CCL8", J. Leukoc. Biol., vol. 74, p. 243-251, Aug. 2003.
Bruehl Hilke et al., "Dual Role of CCR2 During Initiation and Progression of Collagen-Induced Arthritis: Evidence for Regulatory Activity of CCR2+ T Cells," Journal of Immunology, Bd. 172, No. 2, Jan. 2004.
Marlon P. Quinones et al., "The Complex Role of the Chemokine Receptor CCR2 in Collagen-induced Arthritis: Implications for Therapeutic Targeting of CCR2 in Rheumatiod Arthritis," Journal of Molecular Medicine, Bd. 83, No. 9, Sep. 2005.
Schneider, M. et al., "In Vitro and in Vivo Properties of a Dimeric Bispecific Single-Chain Antibody IgG-Fusion Protein for Depletion of CCR2+ Target Cells in Mice," European Journal of Immunology, Bd. 35, No. 3, Mar. 2005.
Bruhl, H. et al., "Pro- and Antiinflammatory Functions of CCR2 in Collagen-induced Arthritis," Zeitschrift Fur Rheumatologies, Bd. 65, No. 1, 2006.
Vergunst Clarissa E. et al., "Modulation of Rheumatoid Arthritis by Targeting the CCR2 Axis: Results of a Randomized, Placebo-Controlled Trial With Anti-CCR2 Blocking Antibodies," Arthritis & Rheumatism, Bd. 54, No. 12, Dec. 2006.
Brodmerkel Carrie M. et al., "Discovery and Pharmacological Characterization of a Novel Rodent-Active CCR2 Antagonist, INCB 3344," Journal of Immunology, Bd. 175, No. 8, Oct. 2005.

(Continued)

*Primary Examiner* — Phuong Huynh
(74) *Attorney, Agent, or Firm* — Birch, Stewart, Kolasch & Birch, LLP

(57) ABSTRACT

The invention relates to the use of an antibody which can specifically bind to chemokine receptor CCR2 for producing a medicament utilized for the treatment of multiple sclerosis and/or rheumatoid arthritis in a subject that is preferably a primate or a human. In another embodiment, the invention relates to the use of an antibody which can specifically bind to chemokine receptor CCR2 for producing a medicament that is utilized for depleting monocytes in subjects suffering from multiple sclerosis and/or rheumatoid arthritis. The invention further relates to corresponding in vitro methods and therapeutic methods. And antibody which binds to CD 14, for example, can be used in addition to the antibody that can bind to CCR2.

18 Claims, 8 Drawing Sheets

(56) References Cited

OTHER PUBLICATIONS

Mack M. et al., "Expression and Characterization of the Chemokine Receptors CCR2 and CCR5 in Mice," The Journal of Immunology, Bd. 166, No. 7, Apr. 2001.

Blanpain et al., "Multiple active states and ologomerization of CCR5 revealed by functional properties of monolconal antibodies", Molecular Biology of the Cell, 2002, vol. 13, pp. 723-737.

Brodmerkel, C. M. et al., "Discovery and pharmacological characterization of a novel rodent-active CCR2 antagonist, INCB3344", The Journal of Immunology, 2005, vol. 175, No. 8, pp. 5370-5378.

Bruhl, H. et al., "Dual role of CCR2 during initiation and progression of collagen-induced arthritis: Evidence for regulatory activity of CCR2+ T cells[1]", The Journal of Immunology, 2004, vol. 172, No. 2, pp. 890-898.

Geissmann, F. et al., "Blood monocytes consist of two principal subsets with distinct migratory properties", Immunity, Jul. 2003, vol. 19, pp. 71-82.

Kurtzke, J. F., "Rating neurologic impairment in multiple sclerosis: An expanded disability status scale (EDSS)", Neurology, 1983, vol. 33, No. 11, pp. 1444-1452.

Mack, M. et al., "Expression and characterization of the chemokine receptors CCR2 and CCR5 in mice", The Journal of Immunology, 2001, vol. 166, No. 7, pp. 4697-4704.

Quinones, M. P. et al., "Experimental arthritis in CC chemokine receptor 2-null mice closely mimics severe human rheumatoid arthritis", The Journal of Clinical Investigation, Mar. 2004, vol. 113, No. 6, pp. 856-866.

Schneider, M. A. et al., "In vitro and in vivo properties of a dimeric bispecific single-chain antibody IgG-fusion protein for depletion of CCR2+ target cells in mice", European Journal of Immunology, 2005, vol. 35, pp. 987-995.

Wong, Lu-Min et al., "Organization and differential expression of the human monocyte chemoattractant protein 1 receooptor gene", The Journal of Biological Chemistry, 1997, vol. 272, No. 2, pp. 1038-1045.

Ziegler-Heitbrock, H. W. L. "Definition of human blood monocytes", Journal of Leukocyte Biology, May 2000, vol. 67, pp. 603-606.

Quinones, Marlon P. et al., "The complex role of the chemokine receptor CCR2 in collagen-induced arthritis: implications for therapeutic targeting of CCR2 in rheumatoid arthritis", Journal of Molecular Medicine, 2005, vol. 83, No. 9, pp. 987-995.

Bruhl, H. et al., "Pro- and antiinflammatory functions of CCR2 in collagen-induced arthritis", Zeitschrift Fur Rheumatologie, vol. 65, No. Suppl. 1, 2006, pp. S77, XP002442230.

Bruhl, H. et al., "Surface expression of CC- and CXC-chemokine receptors on leucocyte subsets in inflammatory joint diseases", Clin. Exp. Immunol, 2001, vol. 126, 551-559.

El-Asmar, L. et al., "Evidence for negative binding cooperativity within CCR5-CCR2b heterodimers", Molecular Pharmacology, 2005, vol. 67, pp. 460-469.

Feterowski, Carolin et al., "CC chemokine receptor 2 regulates leukocyte recruitment and IL-10 production during acute polymicrobil sepsis", European Journal of Immunology, 2004, vol. 34, pp. 3364-3673.

Fife, B. T. et al., "CC chemokine receptor 2 is critical for induction of experimental autoimmune encephalomyelitis", Journal of Experimental Medicine, 2000, vol. 192, No. 6, pp. 899-905.

Izikson, L. et al., "Resistance to experimental autoimmune encephalomyelitis in mice lacking the CC chemokine receptor (CCR)2", Journal of Experimental Medicine, 2000, vol. 192, No. 7, pp. 1075-1080.

Kennedy, K. J. et al., "Acute and relapsing experimental autoimmune encephalomyelitis are regulated by differential expression of the CC chemokines macrophage inflammatory protein-1∝ and monocyte chemotactic protein-1", Journal of Neuroimmunology, 1998, vol. 92, Nos. 1-2, pp. 98-108.

Kivisakk, P. et al., "T-cells in the cerebrospinal fluid express a similar repertoire of inflammatory chemokine receptors in the absence or presence of CNS inflammation: implications for CNS trafficking", Clin. Exp. Immunol., 2002, vol. 129, pp. 510-518.

Mahad, D. J. et al., "The role of MCP-1 (CCL2) and CCR2 in multiple sclerosis and experimental autoimmune encephalomyelitis (EAE)", Seminars in Immunology, 2003, vol. 15, pp. 23-32.

Mahad, D. et al., "Modulating CCR2 and CCL2 at the blood-brain barrier: relevance for multiple sclerosis pathogenesis", Brain, 2006, vol. 129, pp. 212-223.

Maus, U. et al., "The role of CC chemokine receptor 2 in alveolar monocyte and neutrophil immigration in intact mice", Am. J. Respir. Crit. Care Med., 2002, vol. 166, pp. 268-273.

Peters, W. et al., "A mechanism for the impaired IFN-γ production in C-C chemokine receptor 2 (CCR2) knockout mice: role of CCR2 in linking the innate and adaptive immune responses", J. Immunol., 2000, vol. 165, No. 12, 7072-7077.

Salcedo, Rosalba et al., "Human endothelial cells express CCR2 and respond to MCP-1: direct role of MCP-1 in angiogenesis and tumor progression", Blood, 2000, vol. 96, No. 1, pp. 34-40.

Sato, N. et al., "CC chemokine receptor (CCR)2 is required for langerhans cell migration and localization of T helper cell type 1 (Th1)-inducing dendritic cells: Absence of CCR2 shifts the leishmania major-resistant phenotype to a susceptible state dominated by Th2 cytokines, B cell outgrowth, and sustained neutrophilic inflammation", J. Exp. Med., 2000, vol. 192, No. 2, pp. 205-218.

Serbina, N. V. et al., "Monocyte emigration from bone marrow during bacterial infection requires signals mediated by chemokine receptor CCR2", Nature Immunology, 2006, vol. 7, No. 3, pp. 311-317.

Sohy, D. et al., "Allosteric transinhibition by specific antagonists in CCR2/CXCR4 heterodimers", J. Biol. Chem., 2007, vol. 282, pp. 30062-30068.

Steinman, L. "Multiple sclerosis: a coordinated immunological attack against myelin in the central nervous system", Cell, May 1996, vol. 85, No. 3, pp. 299-302.

Zuurman, M. W. "Orphan chemokine receptors in neuroimmunology: Functional and pharmacological analysis of L-CCr and HCR", Dissertation, ISBN: 90-367-1874-0, esp. p. 68.

Wagner, Dissertation 2001, pp. 14-15, 84-89.

Charo et al., Israel F., "Molecular Cloning and Functional Expression of Two Monocyte Chemoattractant Protein 1 Receptors Reveals Alternative Splicing of the Carboxyl-Terminal Tails," Proc. Natl. Acad. Sci. USA, Cell Biology, vol. 91, pp. 2752-2756, Mar. 1994.

"Annual Update 2004/2005—Treatment of Musculoskeletal Disorders," Drugs of the Future 2005, 30(2): 181-232, (2005).

"Annual Update 2004/2005—Treatment of Neurological Disorders," Drugs Fut. 2005, 30(11): 1107-1200, (2005).

Haringman et al., "A Randomized Controlled Trial With an Anti-CCL2 (Anti-Monocyte Chemotactic Protein 1) Monoclonal Anitbod in Patients With Rheumatoid Arthritis," Arthritis & Rheumatism, vol. 54, No. 8, pp. 2387-2392, Aug. 2006.

Han, K.H., et al., "Role of the First Extracellular Loop in the Functional Activation of CCR2," The Journal of Biological Chemistry, vol. 274, No. 45, pp. 32055-32062, (1999).

Canadian Office Action dated May 17, 2013 for Canadian Application No. 2,648,330.

Izikson et al., "Targeting Monocyte Recruitment in CNS Autoimmune Disease," Millennium Award Recipient Contribution, Clinical Immunology, vol. 103, No. 2, May 2002, pp. 125-131.

Abstracts, Zeitschrift für Rheumatologie, vol. 65, Suppl 1, 2006.

Angulo, et al., "Nitric oxide-producing CD11b+Ly-6G(Gr-1)+CD31(ER-MP12)+ cells in the spleen of cyclophosphamide-treated mice: implications for T-cell responses in immunosuppressed mice," Blood, Jan. 1, 2000, vol. 95, No. 1, pp. 212-220.

Belnoue, et al., "Chemokine Receptor CCR2 Is Not Essential for the Development of Experimental Cerebral Malaria," Infection and Immunity, Jun. 2003, vol. 71, No. 6, pp. 3648-3651.

Brühl, et al., Targeting of Gr-1+, CCR2+ Monocytes in Collagen-Induced Arthritis, Arthritis & Rheumatism. vol. 56, No. 9, Sep. 2007, pp. 2975-2985.

Brys, et al., "Reactive Oxygen Species and 12/15-Lipoxygenase Contribute to the Antiprolifeferative Capacity of Alternatively Activated Myeloid Cells Elicited during Helminth Infection," The Journal of Immunology, 2005, 174: pp. 6095-6104.

(56) References Cited

OTHER PUBLICATIONS

Goñi, et al., "Immunosuppression during acute *Trypanosoma cruzi* infection: involvment of Ly6G (Gr1+)CD11b+ immature myeloid suppressor cells," International Immunology, vol. 14, No. 10, pp. 1125-1134, 2002.

Haringman, et al., "A Randomized Controlled Trial With an Anti-CCL2 (Anti-Monocyte Chemotactic Protein 1) Monoclonal Antibody in Patients With Rheumatoid Arthritis," Arthritis & Rheumatism, Aug. 2006, vol. 54, No. 8, pp. 2387-2392.

Maus, et al., "Monocytes Are Potent Facilitators of Alveolar Neutrophil Emigration During Lung Inflammation: Role of the CCL2-CCR2 Axis," The Journal of Immunology, 2003, 170; pp. 3273-3278.

Maus, et al., "CCR2-positive monocytes recruited to inflamed lungs downregulate local CCL2 chemokine levels," AM J Physiol Lung Cell Mol Physiol 288, pp. L350-L358, 2005 (Oct. 2004 first published).

Peters, et al., "CCR2-Dependent Trafficking of F4/80dim Macrophages and CD11cdim/intermediate Dendritic Cells Is Crucial for T Cell Recruitment to Lungs Infected with *Mycobacterium tuberculosis*," The Journal of Immunology, 2004, 172: pp. 7647-7653.

Schneider, Herstellung von murinen bispezifischen Antikörpern zur Depletion von Chemokinrezeptor-positiven Zellen; Dissertation zur Erlangung des Doktorgrades der Fakultät für Chemie und Pharmazie der Ludwig-Maximilians-Universität, München, 2003.

Suzuki, et al., Gemcitabine Selectively Eliminates Splenic Gr-1+/CD11b+ Myeloid Suppressor Cells in Tumor-Bearing Animals and Enhances Antitumor Immune Activity, Clin Cancer Res 2005:11 (18) Sep. 15, 2005, pp. 6713-6721.

Xu, et al., "Differentiation to the CCR2+ Inflammatory Phenotype in Vivo Is a Constitutive, Time-Limited Property of Blood Monocytes and Is Independent of Local Inflammatory Mediators." The Journal of Immunology, 2005, 175: pp. 6915-6923.

European Search Report issued in corresponding European Patent Application 12 16 5439 on May 21, 2012.

Response to Office Action in EP 07 723 870.7 filed on Nov. 27, 2012.

Abbas, et al., "Cellular and Molecular Immunology," Fifth Edition, (2003) p. 494.

Mazzoni, et al., "Myeloid Suppressor Lines Inhibit T Cell Responses by an NO-Dependent Mechanism," The Journal of Immunology, 2002, 168: pp. 689-695.

Huang, et al., "Gr-1+CD115+ Immature Myeloid Suppressor Cells Mediate the Development of Tumor-Induced T Regulatory Cells and T-Cell Anergy in Tumor-Bearing Host," Cancer Res 2006; 66(2): Jan. 15, 2006, pp. 1123-1131.

Serafini, et al., "Derangement of immune responses by myeloid suppressor cells," Cancer Immunol Immunother. 2004, 53: pp. 64-72.

Terabe, et al., "Transforming Growth Factor-B Production and Myeloid Cells Are an Effector Mechanism through Which CD1d-restricted T Cells Block Cytotoxic T Lymphocyte-mediated Tumor Immunosurveillance: Abrogation Prevents Tumor Recurrence," The Journal of Experimental Medicine, vol. 198, No, 11, Dec. 1, 2003, pp. 1741-1752.

Bunt, et al., "Inflammation Induces Myeloid-Derived Suppressor Cells that Facilitate Tumor Progression," The Journal of Immunology, 2006, 176: pp. 284-290.

Makarenkova, et al., "CD11b+/Gr1+ Myeloid Suppressor Cells Cause T Cell Dysfunction after Traumatic Stress," The Journal of Immunology, 2006, 176: pp. 2085-2094.

* cited by examiner

A.

B.

TREATMENT OF MULTIPLE SCLEROSIS AND/OR RHEUMATOID ARTHRITIS

This Application is the National Phase Under 35 U.S.C. §371 of PCT International Application No. PCT/EP2007/002929 which has an International filing date of Apr. 2, 2007, which claims priority to German Application No. 102006015341.3 filed on Apr. 3, 2006. The entire contents of all applications listed above are hereby incorporated by reference.

The present invention relates to the treatment of multiple sclerosis and/or rheumatoid arthritis by means of antibodies.

Multiple sclerosis is a disease of the central nervous system in which the myelin sheaths of the nerve fibers are destroyed, i.e. the nerve fibers are demyelinated. So far, cause and pathophysiology are only poorly understood. Presumably, it is a matter of an exogenously and endogenously modulated immunological process. The symptoms of multiple sclerosis are relatively unspecific and, for example, comprise spastic paralysis and other motor and sensory deficits.

Until now, no satisfactory therapy of multiple sclerosis has been possible. For example, so far, a therapy is carried out by highly-dosed administration of steroids, as well as the administration of azathrioprine, glatiramer acetate, methotrexate, mitoxantrone or by an immunomodulating treatment, e.g. with interferons. However, this only leads to a decrease of the frequency and intensity of the acute phases of the disease. Other than that, the treatment is oriented to the alleviation of the symptoms.

Schneider et al. mention that the depletion of cells which express the chemokine receptor CCR2 could be a possible strategy for the treatment of inflammatory diseases (Schneider, M. A., Brühl, H. Wechselberger, A., et al. (2005), In vitro and in vivo properties of a dimeric bispecific single-chain antibody IgG-fusion protein for depletion of CCR2$^+$ target cells in mice. European Journal of Immunology, vol. 35, p. 987-995). The authors describe the lysis of CCR2-positive cells in mice by means of bispecific antibodies which, among others, is directed against CCR2. However, no therapeutic effect is shown at all.

Rheumatoid arthritis is a chronic inflammatory systemic disease, predominantly affecting the joints, and leading to deformations as well as movement restrictions. Symptoms are, for example, swelling, pain and restricted movement. The cause of rheumatoid arthritis is still unexplained. Among others, an immunopathogenesis as well as infectious causes and genetic factors are considered.

Typically, therapy of rheumatoid arthritis is carried out with the so called antirheumatics, i.e. e.g. with DMARDs (disease modifying antirheumatic drugs) including, for example, methotrexate and leflunomide. In addition, steroids can be used. Furthermore, biologics or immunosuppressant agents such as TNF-alpha blockers (e.g. monoclonal antibodies directed against TNF-alpha or Ethernacept) or IL-1 receptor antagonists (e.g. Anakinra) can be employed. Non-steroidal antirheumatic drugs (NSAR) are predominantly employed for analgesic therapy. Still, in many cases, it is not possible to satisfyingly treat the disease and to avoid damages to joints which can even result in immobilization.

Brühl et al. describe the administration of monoclonal antibodies (MC-21) which are directed against the chemokine receptor CCR2 in the mouse model of collagen-induced arthritis (Brühl H, Cihak J, Schneider M A, Plachy J, Rupp T, Wenzel I, Shakarami M, Milz S, Ellwart J W, Stangassinger M, Schlondorff D, Mack M. (2004) Dual role of CCR2 during initiation and progression of collagen-induced arthritis: evidence for regulatory activity of CCR2+ T cells. J. Immunol., vol. 172(2), p. 890-898). The authors describe that an alleviation of arthritis by means of the antibody was only achieved when the blockade of CCR2 occurred during the initiation phase of the disease (that is directly after the immunization with collagen and before the occurrence of joint inflammation), but not during the progression phase. During the progression phase, the blockade of CCR2 even causes an aggravation of arthritis and of the immune response against collagen. From that it can be concluded that by means of the antibody solely the artificial generation of the disease in the model system was influenced, that is the immunization of the animal with collagen. Yet, the treatment of the disease itself does not appear possible in this way.

Brodmerkel et al. (2005) describe a small molecule antagonist, INCB3344, of the mouse CCR2 receptor (Brodmerkel, C. M., Huber, R. Covington, M., Diamond, S., Hall, L., et al. (2005). Discovery and Pharmacological Characterization of a Novel Rodent-Active CCR2 Antagonist, INCB3344). The molecule was studied in the mouse model of the experimental autoimmune encephalitis (EAE), a model of multiple sclerosis. However, the administration started already at a point in time (0 days and 7 days after immunization, respectively) at which only a few animals showed clinical signs of the disease. Brodmerkel et al. (2005) further describe the administration of INCB3344 in rats in the model of adjuvant-induced arthritis. Again, the administration already started at a point in time (9 days after immunization) at which the rats did not show any or only minor clinical signs of the disease.

In summary, one can conclude that currently there is no satisfactory therapy for multiple sclerosis and/or rheumatoid arthritis.

Against this background, it is an object of the present invention to provide a new possibility of treatment for multiple sclerosis and/or rheumatoid arthritis.

This object is solved by a medicament containing an antibody which can specifically bind to the chemokine receptor CCR2 for the treatment of multiple sclerosis and/or rheumatoid arthritis in a subject and the use of said antibody for the manufacture of a medicament for the treatment of multiple sclerosis and/or rheumatoid arthritis in a subject, respectively.

Surprisingly, it was found in the context of the present invention that the administration of antibodies directed against CCR2, as opposed to the hitherto existing opinion in the literature (see in particular Brühl et al. (2004), as cited above), can effect a clinical improvement of multiple sclerosis and/or rheumatoid arthritis. That is to say, it was found that by administering antibodies directed against CCR2, a clinical improvement of rheumatoid arthritis can very well be achieved, preferably at a dosage which is lower than the dose chosen by Brühl et al. (2004). Likewise, it was found that a clinical improvement of multiple sclerosis can be effected.

Furthermore, it was surprisingly found that a treatment is not only possible during the initiation of the disease in an animal model, but also when explicit clinical symptoms of the disease are already present. This allows for a relatively late therapeutic intervention, among others, as it is required in human clinical practice.

The chemokine receptor CCR2 is known to a person skilled in the art (see, for example, entry no. 601267 in the database Online Mendelian Inheritance in Man (see OMIM on the website of the National Institute of Health, USA)). This receptor is a chemokine receptor of the CC type which exists in two different splice variants in humans, CCR2A and CCR2B (Wong, L.-M., Myers, S. J., Tsou, C.-L., et al. (1997) Organization and Differential Expression of the Human Monocyte Chemoattractant Protein 1 receptor gene: Evidence for the role of the Carboxyl-Terminal Tail in Receptor Trafficking. J. Biol. Chem., vol. 272, p. 1038-1045). The molecule is also known under the name human monocyte chemoattractant protein-I receptor gene. This receptor is a 7-transmembrane domain G-protein-coupled receptor. The corresponding orthologs of CCR2 from several other species are also known and can easily be determined by a person skilled in the art, for example, by means of sequence searches starting from the human CCR2.

The term antibody is known to a person skilled in the art. According to the present invention, the term antibody is to be understood in a broad scope and, among others, comprises polyclonal, monoclonal and recombinantly produced antibodies as well as fragments thereof, such as Fv, Fab, and F(ab)2 fragments, which can be single-stranded (single-chain). Preferably, the antibody is of the isotype IgG. Preferably, the antibody is of an isotype which is capable of inducing effector mechanisms such as ADCC (antibody-dependent cellular toxicity) or complement activation. This would, for example, be the case for human IgG1 or mouse IgG2a. Preferably, the antibody is such that it is, if possible, not or only to a low extent rejected by the immune system of the subject. This can, for example, be achieved by forming the regions (e.g. the Fc regions) which are not required for recognizing the antigen (here: the CCR2 receptor) from antibody sequences of the species of the subject. For example, so-called humanized antibodies are known to a person skilled in the art which are particularly suitable for application in humans. Antibodies which are otherwise modified, e.g. bispecific antibodies (see, for example, Schneider et al. (2005), already cited above), diabodies, as well as so-called binders or aptamers, which can, for example, be made by means of a peptide backbone or a nucleic acid backbone, for example a RNA, are also comprised by the term antibody in the context of the present invention. Preferably, antibodies in the context of the present invention have a molecular weight of less than 600 kDa, more preferably of less than 300 kDa, still more preferably of less than 200 kDa, and most preferably of about 150 kDa. The production of suitable polyclonal, monoclonal and recombinant antibodies, including the production of binders and aptamers, is known to a person skilled in the art (see, for example, Jörg Knäblein (editor), Modern Biopharmaceuticals, vol. 2, p. 635), see also the example. For example, the immunization can be carried out by injection of cells expressing the CCR2 receptor. This has the advantage that the receptor is used as an antigen in its native fold. Furthermore, an immunization with peptide fragments of the antigen is possible. Preferably, corresponding peptides are chosen from the extracellular domain of CCR2, in particular from the first two loops. An identification of suitable antibodies (including binders and aptamers) is also possible via the screening of libraries with corresponding molecules or cells expressing these molecules, e.g. by means of phage display. After the identification, the antibodies (including binders and aptamers) can be produced by means of methods that are known to a person skilled in the art.

Preferably, the antibodies of the invention are coupled to domains which enhance the depleting effect of the antibodies. Such domains are known to the person skilled in the art. An example for that is an Fc domain inducing ADCC or complement activation. Another possibility is the coupling of an antibody to a toxin. The antibody can also be a bispecific antibody such as the bispecific variant of MC-21, which is described in Schneider et al. (2005) and which recognizes mouse CD3-epsilon as a second antigen (Schneider et al., (2005), already cited above).

The antibody according to the present invention can bind to the chemokine receptor CCR2. Preferably, the antibody binds to loop1 and loop2 of the extracellular CCR2 domains. Preferably, the antibody binds with a dissociation constant Kd of $10^7$ M or more, more preferably of $10^8$ M or more, even more preferably of $10^9$ M or more, most preferably of $10^{11}$ M or more. Preferably, the binding is specific. Specific binding in the context of the present invention means that under physiological conditions (that is, for example, in physiological salt solution, in cell culture or in vivo, preferably in the blood or tissue of the corresponding subject) the antibody binds to CCR2 with at least 10-fold affinity, preferably 20-fold affinity, more preferably 50-fold affinity, most preferably 100-fold affinity to CCR2 as compared to other proteins, in particular, as compared to similar proteins (e.g. as compared to CCR5, CCR1, CCR3, or other chemokine receptors and G-protein-coupled receptors with 7 transmembrane domains, preferably as compared to CCR5). However, a binding to other proteins can be tolerable as far as it does not interfere with the therapeutic effect of the antibody. Yet, cross-reactivity with orthologous CCR2 receptors from other species is possible and can even be advantageous in order to allow an application of the antibody in several species. Such cross-reactivity is not uncommon and it is known to the person skilled in the art how to determine the cross-reactivity. Further details regarding this matter can also be taken from the example.

Preferably, the antibody to be used according to the invention can inhibit the chemokine receptor CCR2. It can easily be determined whether an antibody inhibits the chemokine receptor CCR2. For example, such antibody decreases MCP-1- and MCP-3-induced chemotaxis of cells, which react chemotactically by means of CCR2, e.g. monocytes. Examples of corresponding cells from mouse or human, respectively, are Monomac6 cells or human monocytes from peripheral blood (PBMC), respectively. The corresponding assay is described in the example.

Furthermore, the inhibition of the chemokine receptor CCR2 can be determined by the fact that an inhibition of the binding of MCP-1 and of the calcium influx induced by MCP-1 occurs. A corresponding assay is described in the example.

Examples for antibodies which are suitable or can resemble a starting point for modified antibodies are the antibodies of the group consisting of DOC-1, DOC-2, DOC-3 and MC-21. The production of the antibodies DOC-1, DOC-2, DOC-3 as well as their features are described in the example.

The medicament according to the invention contains the antibody. In addition, the medicament can contain any type of adjuvant which the person skilled in the art considers adequate. Such adjuvants can, for example, be carrier substances such as starch, lactose, fats, stearic acid, alcohol, physiological saline solutions or other additives. In particular, adjuvants which stabilize antibodies and preserve come into consideration.

The administration of the medicament can be carried out with any known method with which the antibody contained in the medicament can be inserted into the target cells, i.e. in particular monocytes, in vitro or in vivo. For example, the medicament can be administered by injection, e.g. intravenously (i.v.), subcutaneously (s.c.), or intraperitoneally (i.p.) in form of solutions or infusions. However, also other modes of administration, such as in microencapsulated form or in form of implants, are conceivable. Preferably, the administration of the medicament is carried out such that the antibody can enter into the circulation or into the respective target area. Also conceivable is an administration directly into the target area, for example, in case of multiple sclerosis into the central nervous system, e.g. the cerebral spinal fluid, or in case of rheumatoid arthritis into the affected joints.

The diseases multiple sclerosis and rheumatoid arthritis are known to the person skilled in the art and have already been described in the introduction.

The term treatment is also known to the person skilled in the art. In the context of the present invention, a treatment concerns any kind of intervention causing a clinical improvement of multiple sclerosis and/or rheumatoid arthritis in a subject. A clinical improvement can, for example in multiple sclerosis, for example be determined by measuring the decrease of neurological deficits, e.g. the palsy. In rheumatoid arthritis, a clinical improvement can e.g. be determined by a reduction of the symptoms, e.g. the swelling, the inflammation or the pain. Preferably, an improvement manifests itself in an alleviation of the clinical symptoms which, for example, correspond to an improvement of a EAE score according to the example of at least 0.25 units, preferably 0.5 units, more preferably at least 0.75 units, most preferably at least 1.0 units. Preferably, the improvement manifests itself in an alleviation of the clinical symptoms which, for example, corresponds to an improvement of the arthritis score according to the example of at least 0.25 units, preferably at least 0.5 units, more preferably at least 0.75 units, more preferably at least 1.0 units, most preferably at least 1.25 units. For an estimation of the clinical improvement in man, many parameters are known as well, for example the EDSS score for multiple sclerosis (Expanded Disability Status Scale, see Kurtzke, J F (1983). Rating neurologic impairment in multiple sclerosis: an expanded disability status scale (EDSS). Neurology, vol. 33(11), p. 1444-1452)). That way, the clinical improvement can manifest itself in an alleviation of the symptoms which, for example, corresponds to an improvement according to the EDSS score of at least 0.5, preferably of at least 1.0, more preferably at least 1.5 units, more preferably at least 2.0 units, most preferably at least 2.5 units. Furthermore, the ACR (American College of Rheumatology) score for rheumatoid arthritis is known for the estimation of the clinical improvement in man.

Preferably, the treatment concerns a subject suffering from multiple sclerosis and/or rheumatoid arthritis. In particular, the treatment relates to multiple sclerosis and/or rheumatoid arthritis during the disease, in particular the treatment in presence of clinical signs of the disease. Clinical signs of the disease, for example, correspond to an EAE-score (see example) of 1.0 or greater, preferably 1.5 or greater, even more preferably 2.0 or greater, even more preferably 2.5 or greater, in particular 3.0 or greater. Clinical signs of the disease, furthermore, correspond, for example, to an arthritis score (see example) of 1.0 or greater, more preferably 2 or greater, even more preferably 3 or greater, even more preferably 4 per paw. For the estimation of the clinical signs in humans, many parameters are known as well, for example the EDSS score (Expanded Disability Status Scale, see Kurtzke, J F (1983). Rating neurologic impairment in multiple sclerosis: an expanded disability status scale (EDSS). Neurology, vol. 33(11), p. 1444-1452)) as well as the ACR (American College of Rheumatology) score for rheumatoid arthritis.

Furthermore, the treatment can, in particular, concern a therapy-refractory multiple sclerosis and/or rheumatoid arthritis, i.e. a form of the respective disease, in which a clinical improvement could not be achieved with the hitherto known agents. In a considerable number of subjects the course of the disease is such that no clinical improvement is possible any longer with the hitherto known agents. Furthermore, the treatment may concern a subject with the respective disease, in which undesired side effects occur to a non-acceptable extent with the hitherto existing treatment methods. The treatment may also concern the respective disease in an advanced stage.

The subject in the context of the present invention is a vertebrate, preferably a mammal. A mammal can, for example, be a rodent (e.g. mouse, rat or rabbit), a pig, a dog, a cat or primate. Preferably, the mammal is a primate (for example, a macaque or a common marmoset or a human). Particularly preferred, the subject is a human.

Usually, an effective dose is determined for the administration of the medicament. The term effective dose and the determination of the effective dose is known to a person skilled in the art, furthermore, a person skilled in the art can go back to the information provided herein for determining the effective dose. A dose is understood to be effective which leads to a clinical improvement of the disease which is treated. In particular, in the context of the present invention, a dose of the medicament which effects an alleviation of the symptoms of multiple sclerosis and/or rheumatoid arthritis in a subject is understood to be an effective dose. An effective dose is, for example, a dose which is chosen such that at least 20%, preferably at least 30%, more preferably at least 40%, most preferably at least 50% of the CCR2-expressing monocytes in the peripheral blood are depleted. Here, a depletion of monocytes is understood to be a destruction of the cells.

Preferably, the effective dose of the medicament is chosen such that it resembles the lowest dose providing for a satisfactory success of treatment of multiple sclerosis and/or rheumatoid arthritis. A particularly suitable effective dose can be determined by continuing to increase the dose in test series until the desired ratio of effect to undesired side effects has been reached. In the context of the present invention, this will, for example, be the case when the disease, which is treated, is no longer further improved clinically upon a further increase of the dose (as the case may be, is even aggravated) and/or when undesired side effects relative to the therapeutic effect are no longer acceptable.

For example, a dose would need to be considered which does not exceed that dose which is required to achieve a depletion of 99%, preferably 98%, more preferably 95%, more preferably 90%, more preferably 80%, more preferably 70%, even more preferably 50% of the CCR2-expressing monocytes in the peripheral blood. In the context of the invention, it could be shown that the dose, although causing an extensive depletion of the monocytes, yet not being considerably higher, causes a remarkable clinical improvement and not an aggravation of the disease. In particular, this relates to rheumatoid arthritis.

Alternatively, the dose can be estimated based on whether it causes a release of interleukin-6 (IL-6) and/or interleukin-4 (IL-4). The estimate of the dose can, in particular, be based on the release of IL-6. That way, the dose can preferably be chosen such low that it does not cause an excessive release of IL-6 and/or IL-4. For example, the dose can be chosen such that it does not cause more than a 20-fold increase, preferably not more than a 10-fold increase, more preferably not more than a 5-fold increase, most preferably not more than a 2-fold increase of the level of IL-6 and/or IL-4 in the blood plasma. In this context, the increase relates to the normal level of IL-6 and/or IL-4 in the blood plasma of the subject. The level the subject has before the administration of the medicament was carried out is preferably regarded as "normal" level of IL-6 and/or IL-4 in this context. It is known to the person skilled in the art, when a release of IL-6 and/or IL-4 can be considered as being effected by the administration of the medicament. It should be possible to regard an increase of the level of IL-6 and/or IL-4 two to six hours after intraperitoneal injection of the antibody as being effected by the medicament.

Moreover, a dose is to be regarded as a suitable dose, the upper limit of which optionally corresponds to 0.01; 0.02; 0.03; 0.05; 0.07; 1.0; 1.5; 2.0; 2.5; or 3.0 mg of the antibody per kg body weight of the subject per day, and the upper limit of which optionally corresponds to 1.0; 1.5; 2.0; 2.5; 3.0; 4.0; 5.0; 7.0; 10; 12; 14; 17; or 20 mg of the antibody per kg body weight of the subject per day, wherein said limits may be combined with each other in any way, wherein they are, yet, selected such that a positive range is enclosed by the limits. Examples for such ranges are 0.01-20 or 0.01-2 or 2.5-20 mg of the antibody per kg body weight of the subject per day.

Furthermore, the present invention relates to a medicament containing an antibody which can bind to the chemokine receptor CCR2 in multiple sclerosis and/or rheumatoid arthritis in a subject and the use of said antibody for the manufacture of a medicament for depleting monocytes in multiple sclerosis and/or rheumatoid arthritis in a subject, respectively.

Moreover, the present invention relates to a medicament containing an antibody which is capable of depleting monocytes in multiple sclerosis and/or rheumatoid arthritis in a subject and the use of said antibody for the manufacture of a medicament for the treatment of multiple sclerosis and/or rheumatoid arthritis in a subject, respectively.

All preferred embodiments and variants of the invention and definitions illustrated in this description self-evidently also relate to the two aforementioned medicaments and uses in a corresponding manner.

In the context of the present invention, it was found that the administration of an antibody which is able to inhibit the chemokine receptor CCR2 can effect a depletion of CCR2-expressing monocytes.

The present inventors assume that the treatment of multiple sclerosis and/or rheumatoid arthritis preferentially occurs via a depletion of CCR2-expressing inflammatory monocytes.

In the context of the present invention, the depleting of monocytes is understood to be the destruction of the corresponding monocytes.

The mechanism of the depletion can be influenced by the design of the antibody. Preferably, the depletion is effected by a mechanism of cell lysis based on ADCC (antibody dependent cellular toxicity) and/or complement activation. Yet, in case of complement activation, it should be paid attention to the fact that no increased inflammatory reaction, e.g. via the complement molecules C3a and C5a, occurs. The depletion based on ADCC can, for example, be mediated via CD16/32 or CD64. ADCC makes it possible that monocytes deplete each other.

A depletion with the help of an antibody of the invention can be achieved in various species. For instance, the monocyte populations of mouse and man are similar. It is, for example, known that also in the mouse a dichotomy of the blood monocytes into inflammatory ($CD11b^+$ $CCR2^+$ $GR1^+$ $CD62L^+$ $CX_3CR_1^{low}$) and non-inflammatory ($CD11b^+$ $CCR2^-$ $GR1^-$ $CD62L^-$ $CX_3CR_1^{high}$) monocytes can be observed (Geissmann F, Jung S, Littman D R. (2003). Blood monocytes consist of two principal subsets with distinct migratory properties. Immunity, vol. 19(1), p. 71-82.). In humans, these two monocyte populations have already been known for a longer time and are predominantly determined via the expression level of the surface markers CD14 and CD16 (Ziegler-Heitbrock H W (2000). Definition of human blood monocytes. J Leukoc Biol., vol. 67(5), p. 603-6.).

In a further embodiment, other than the antibody directed against CCR2, at least one antibody which is specific for monocytes, preferably selected from the group consisting of CD14, CD33, CD64, CD68, CD91, CD115, and CD163, can additionally be used for the treatment. Particularly preferred is CD14. Such an embodiment can be of particular advantage when the subject is a primate, in particular a human.

In another embodiment, the present invention relates to a method for depleting monocytes comprising contacting the monocytes with an antibody which can specifically bind to the chemokine receptor CCR2. Here, methods can be excluded that represent a surgical or therapeutic treatment of the human or animal body. Preferably, the contacting is carried out in vitro. The term "in vitro" is understood in its broadest possible form in this context. It relates to any method that takes place outside of the living body, that is particularly also to methods in cell culture, tissue culture or organ culture. The term "in vitro" is particularly understood to also comprise a method that relates to the treatment of blood outside the body of the subject.

The present invention further relates to a method for the treatment of multiple sclerosis and/or rheumatoid arthritis in a subject comprising the step of administering an antibody that can specifically bind to the chemokine receptor CCR2.

The present invention further relates to a method for the depletion of specific monocytes in a subject comprising the step of administering an antibody that can specifically bind to the chemokine receptor CCR2.

All of the preferred implementations and variants of the invention and definitions that have already been presented above, self-evidently also relate to the two aforementioned methods in the corresponding manner.

Figure 1:
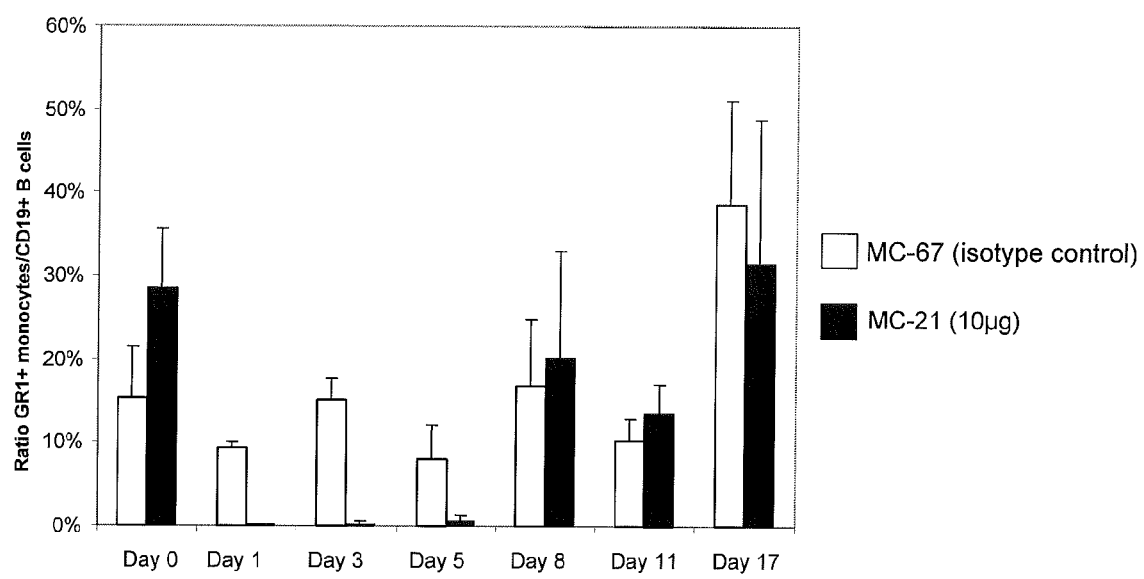
FIG. 1

Kinetics of monocyte depletion. A daily injection of 10 µg MC-21 or isotype control antibody, respectively, lead to depletion of GR1+ monocytes from the peripheral blood of mice for at least 5 days. 5 mice per group were examined. The withdrawals of blood took place about 7 hours after the antibody injections. Based on the ratio of GR1+ monocytes to CD19+ B cells (which are not essentially influenced by the antibody treatment), one can recognize the depletion of the GR1+ monocytes by the MC-21 antibody, which persists for at least 5 days. day, Tag

FIG. 2

At high concentration, MC-21 induced a release of IL-6. C57BL/6-mice were intraperitoneally treated with 100 µg or 10 µg MC-21 antibodies. 2 hours after the injection, the IL-6 levels in the plasma were measured by means of ELISA (enzyme-linked immuno-sorbent assay). Only at high doses, the MC-21 antibody lead to the release of IL-6. anti-CCR2, MC-21 antibody; i.p., intraperitoneally

FIG. 3

A. Different MC-21 concentrations differentially modulated the course of arthritis. In the model of the collagen-induced arthritis (immunization of DBA/1 mice with 100 µg collagen each on day 1 in complete Freund's adjuvant and on day 21 with incomplete Freund's adjuvant) the daily administration (day 21-32) of highly-dosed MC-21 antibody (50 µg) lead to a clear worsening of arthritis, whereas the daily administration of MC-21 in low dose (10 µg) lead to a clear improvement of arthritis.

B. The daily low-dose administration of the MC-21 antibody (anti-CCR2) (10-20 µg/day i.p.) was also therapeutically effective in the model of collagen-induced arthritis, when the arthritis was already clearly advanced. The mice were immunized twice at an interval of 3 weeks with collagen (200 µg in complete or incomplete Freund's adjuvant, respectively). Not until after the occurrence of clear signs of arthritis (score 3), the antibody treatment was started (day 0). The administration of MC-21 resulted in a standstill of the disease, whereas the disease clearly proceeded in the control group (administration of MC-67). The difference between the MC-21 and MC-67 group was significant (p<0.05 for the days 1-6). The increase of arthritis calculated from day 0 was highly significant within the MC-67 group. Within the MC group, the alteration of the arthritis was not significant.

FIG. 4

The depletion of inflammatory monocytes improved the course of experimental autoimmune encephalomyelitis (EAE) as an animal model of multiple sclerosis. The application of 20 μg MC-21, but not of its isotype control (IgG2b), significantly improved the course of the disease. The MC-21 antibody or the isotype control were administered daily starting from day 17 (peak of the disease) until day 34 after immunization, A clinical degree of severity (score) of 2.5 corresponds to a clear weakness of the hind leg in combination with a unilateral paralysis of the hind leg. A score of 1.0 corresponds to a tail paralysis upon preserved power/motor function of the hind legs. daily; clinical EAE score; days after immunization

FIG. 5

A lesser damage to myelin during the EAE in mice treated with MC-21 35 days after immunization. Quantification of demyelination. MC-21-treated animals had clearly more preserved myelin. IgG2b, isotype control; demyelination

FIG. 6

The injection of antibodies DOC-2 and DOC-3, as opposed to injection of an isotype control antibody (5 mg/kg body weight each) lead to a reduction in the number of CCR2-positive monocytes in the peripheral blood of common marmosets. The relative proportion of CCR2-positive monocytes referred to the total number of leukocytes is depicted, wherein this value was normalized to 100% in the group treated with isotype control antibodies for the respective days. $CCR2^+$ peripheral blood monocytes; injected antibody at 0 h; isotype-control

FIG. 7

The depletion of inflammatory monocytes in non-human primates resulted in the stabilization of the weight (A.) as well as in a reduction of the neurological deficits (B.). Adult female marmosets (*Callithrix jacchus*) were treated with the anti-human CCR2 antibody DOC-2 and with the isotype antibody (IgG1) (5 mg/kg i.p.), respectively. The application of the antibody was started as soon as the first unambiguous neurological symptoms manifested in the animals. Subsequently, the marmosets were treated every two days.

FIG. 8

The therapeutic administration of the anti-human CCR2 antibody resulted in a significantly prolonged lifetime, when the treatment was initiated at the peak of the disease. Adult female marmosets (*Callithrix jacchus*) were treated with the anti-human CCR2 antibody DOC-2 (anti-CCR2, 5 mg/kg i.p., n=2) and PBS (n=2), respectively, starting at the peak of the disease and thereafter every two days until death.

In the following example, the invention is illustrated in more detail, but this is not to be considered as a limitation of the scope of the invention.

EXAMPLE

The MC-21 antibody as a means for the depletion of the inflammatory monocytes in vivo: The monoclonal antibody MC-21 (Mack, M, Cihak J, Simonis C, et al. Expression and characterization of the chemokine receptors CCR2 and CCR5 in mice. J. Immunol. 2001 vol. 166(7), pp. 4697-704) specifically binds to murine CCR2 and does not show any cross-reaction with the closely related murine CCR5 receptor. It showed a strong binding to monocytes wherein the sub-population of the GR1+ monocytes in the mouse is recognized by the antibody.

Effect and kinetics of the MC-21 antibodies in vivo: A singular intraperitoneal injection of the MC-21 antibody into C57BL/6 mice resulted in an almost complete depletion of the inflammatory sub-population of the monocytes (CCR2+ GR1+ monocytes) from blood and spleen (FIG. 1). Depending on the injected dose of MC-21, the depletion of the monocytes persisted for different periods of time. When 5-10 μg were injected, after 24 hours we still observed a complete depletion of the GR1+ monocytes, whereas after 48 hours an appearance of GR1+ monocytes was already noted again. Upon injection of a higher dose of MC-21 (100 or 500 μg), a monocyte depletion persisting for 2-3 days occurred (corresponding to the longer presence of the antibodies in the plasma). By repeated injections of MC-21 antibody, a depletion of monocytes could be maintained for about one week (FIG. 1). After that, a loss of the CCR2 binding ability of the MC-21 antibody occurred due to the appearance of inhibiting mouse anti-rat antibodies. The MC-21-mediated depletion of GR1+ monocytes was predominantly mediated by Fc receptor, since a simultaneous injection of antibodies against the Fc receptors FcgRIII and FcgRII via anti-CD16/32 (clone 2.4G2 ATCC HB197), reduced the MC-21-mediated depletion in blood and spleen. It is assumed that the portion of the MC-21-mediated monocyte depletion which cannot be inhibited by CD16/32 antibody is either based on a complement-dependent mechanism or on an ADCC mechanism depending on CD64.

Figure 2:
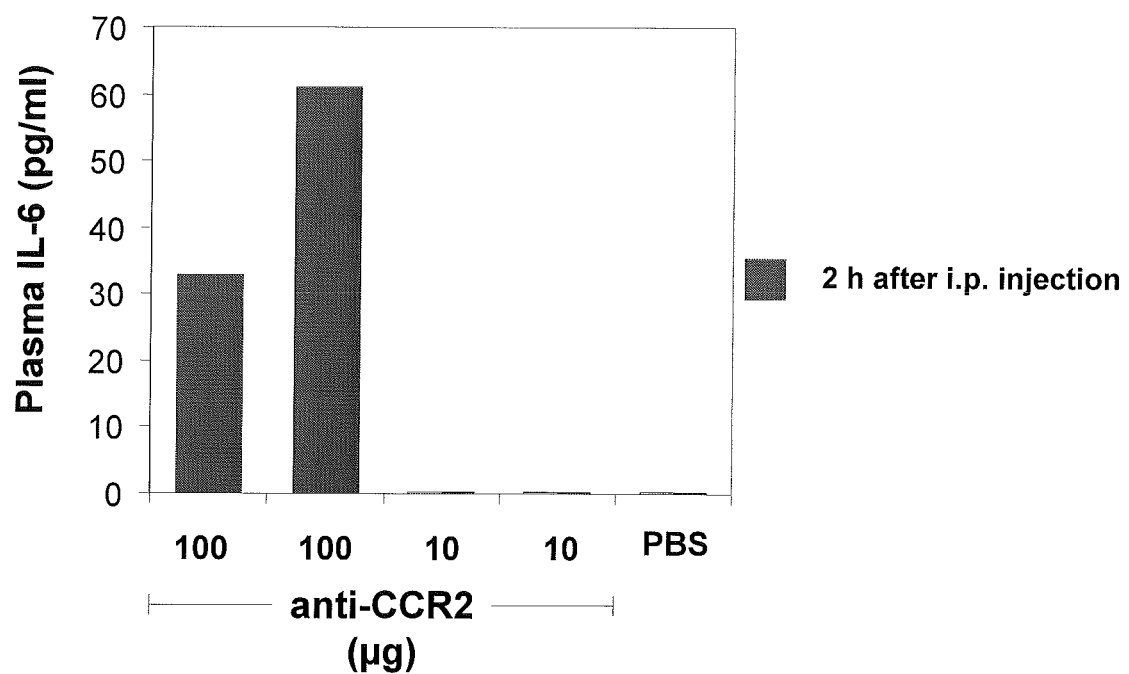

The MC-21 antibody also showed effects on CCR2-expressing basophilic granulocytes. Incubation of complete murine bone marrow with the MC-21 antibody caused a considerable release of IL-6. This IL-6 release was dependent on basophilic granulocytes, since the depletion of the basophilic granulocytes from the complete bone marrow resulted in a considerably reduced MC-21-induced IL-6 release. Also, isolated basophilic granulocytes (isolation by means of magnetic beads directed against DX-5 and subsequent FACS-sorting by means of CD45 and DX-5 expression) were stimulated to release IL-6 by incubation with MC-21 antibodies. Basophilic granulocytes of CCR2-deficient mice were not stimulated to release IL-6 by means of MC-21. These data show that MC-21 induced an activation of basophilic granulocytes and that this activation occurred via binding of MC-21 to CCR2. Since basophilic granulocytes also showed a strong expression of immunoglobulin Fc receptors (in particular CD16/32), we assume that these receptors are important for the immobilization of MC-21 and, possibly, also contribute to the activation of basophils. In vivo, the activation of basophilic granulocytes was dependent on the administered dose of MC-21. Upon injection of 10 μg MC-21, we observed no IL-6 release in vivo, whereas upon injection of 100-500 μg, a clear release of IL-6 was induced (FIG. 2).

Since a depletion of monocytes could already be achieved with low MC-21 doses (e.g. 5-10 μg), and since IL-6 had unfavorable effects on the development of an arthritis, this resulted in the possibility to effect a monocyte depletion without a simultaneous activation of basophils via MC-21 by means of repeated injection of MC-21 in low dosage.

For the analysis, the model of collagen-induced arthritis (CIA) in male DBA/1-mice was used, a model which resembles the human rheumatoid arthritis (RA) in many aspects, and which is employed for the pre-clinical development of important therapies that are currently used in the clinical practice. In the model of collagen-induced arthritis, the arthritis is induced by singular (day 1) or double (day 1 and day 21) immunization with predominantly bovine collagen.

The treatment with antibodies directed against CCR2 from day 1 of the disease model interfered with the immunization with collagen and, therefore, the joint inflammation occurred to a lesser extent. As opposed to the inhibiting effect of anti-CCR2 antibodies, at the point of the primary immunization with collagen, the application of the blocking CCR2 antibody MC-21 in increased concentration (500 µg/mouse every three days) at a later point (from day 4, day 9 or day 21) resulted in a significant worsening of the clinical and histological degree of severity. This effect came along with an increased humoral immune response to collagen (significantly higher anti-collagen antibody titers). Also, CCR2-deficient mice, which were back-crossed to the CIA-susceptible strain DBA/1, showed an increased arthritis (Quinones M P, Ahuja S K, Jimenez F, Schaefer J, Garavito E, Rao A, Chenaux G, Reddick R L, Kuziel W A, Ahuja S S (2004). Experimental arthritis in CC chemokine receptor 2-null mice closely mimics severe human rheumatoid arthritis. J Clin Invest., vol. 113(6), p. 856-66.). These data suggest that the inhibition of CCR2 after induction of arthritis or the lack of CCR2 during the complete course of the disease resulted in a considerable intensification of the arthritis. According to the state of the literature, CCR2 was therefore to be assessed as an unapt target for the treatment of inflammatory rheumatic diseases.

Figure 3:
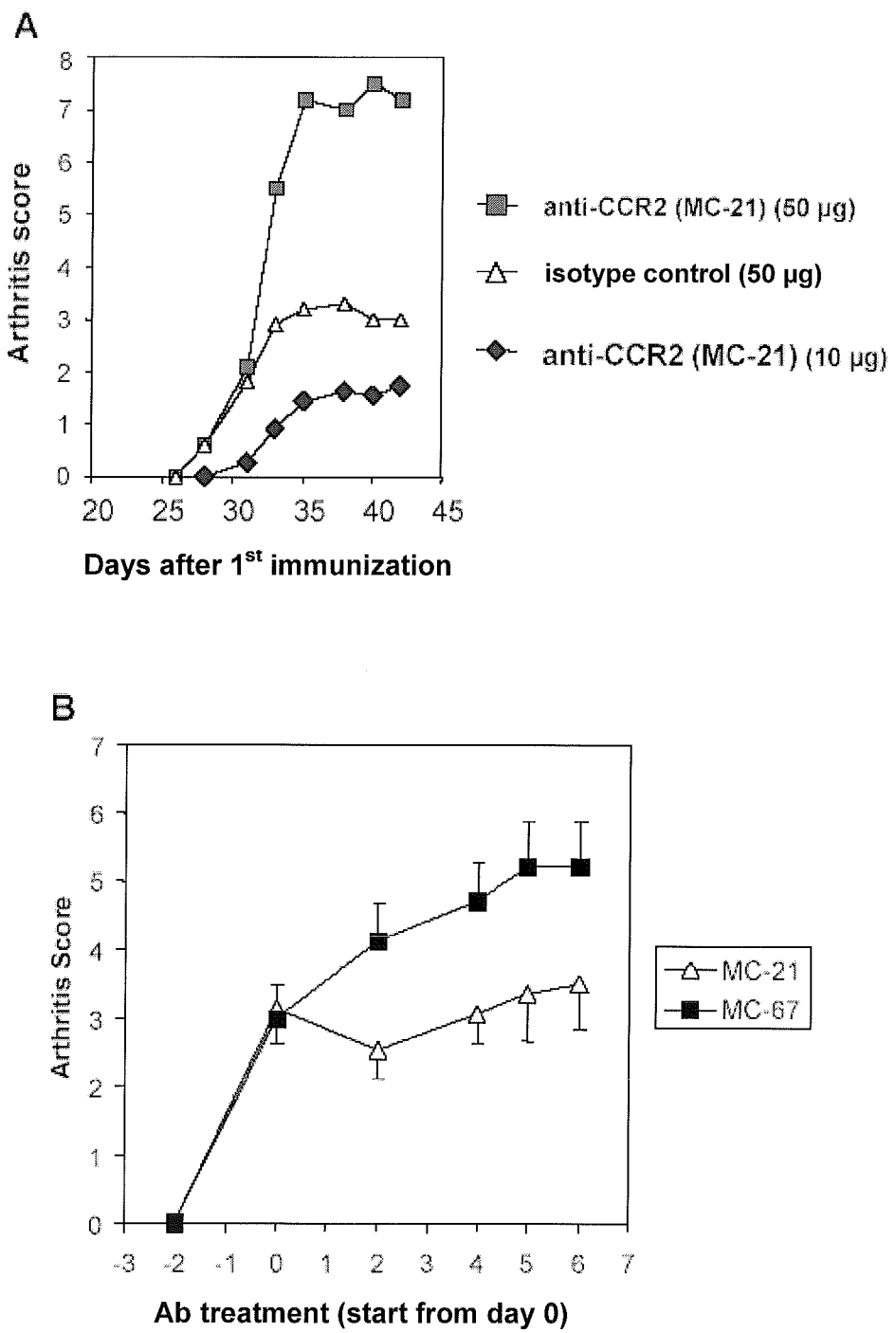

Surprisingly, it could now be shown in the context of the invention (FIG. 3A) that a treatment with low-dose MC-21 antibodies (here, 10 µg intraperitoneally per day) leads to a clear improvement of arthritis also during the progression phase of the collagen-induced arthritis. MC-21 antibodies were only given starting from day 21. In comparison to that, the daily treatment from day 21 with a higher dose of MC-21 (50 µg/day) resulted in a clear aggravation of the arthritis. An administration of antibodies against IgE (from day 21), which leads to an activation of basophilic granulocytes, caused a clear aggravation of arthritis as well.

Monocyte depletion in the MS model: In the animal model of MS, the experimental autoimmune encephalomyelitis (EAE), the disease could be induced by various myelin components (e.g. $MOG_{35-55}$) or by adoptive transfer of autoreactive T cells against these components.

In another work, it was shown that a selective small molecule CCR2-antagonist positively influences the course of the EAE, if it is given before the occurrence of stronger symptoms of the disease (Brodmerkel C M, Huber R, Covington M, Diamond S, Hall L, Collins R, Leffet L, Gallagher K, Feldman P, Collier P, Stow M, Gu X, Baribaud F, Shin N, Thomas B, Burn T, Hollis G, Yeleswaram S, Solomon K, Friedman S, Wang A, Xue C B, Newton R C, Scherle P, Vaddi K (2005). Discovery and pharmacological characterization of a novel rodent-active CCR2 antagonist, INCB3344. J. Immunol., vol. 175(8), p. 5370-8.). In Brodmerkel et al., the underlying mechanism could possibly be a reduced migration of monocytes to the brain. Yet, it may be doubted whether an inhibition of the monocyte migration to the brain is still therapeutically effective, when, at a later stage of the disease, a large number of monocytes is already present in the brain. Therefore, the results of Brodmerkel appear to be due to a manipulation of the artificial initiation of the disease in the model system. Surprisingly, it was now shown within the context of the invention that a treatment regime based on CCR2 is effective as a therapeutic in the EAE stage of the progression or effector phase, i.e. during the disease.

Figure 4:
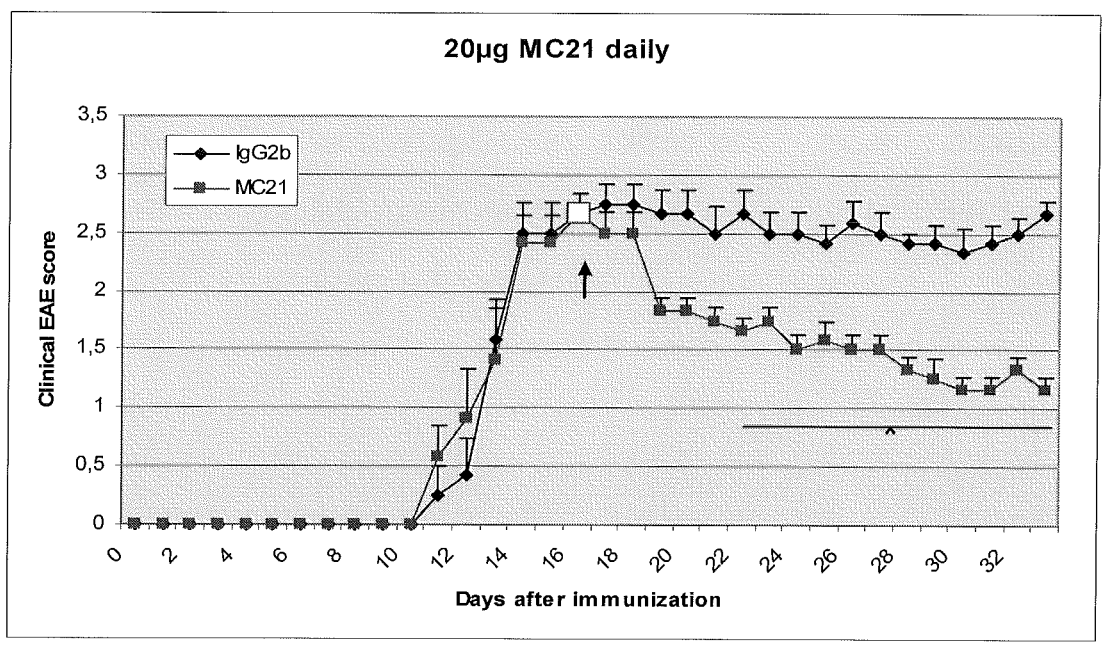
Figure 5:
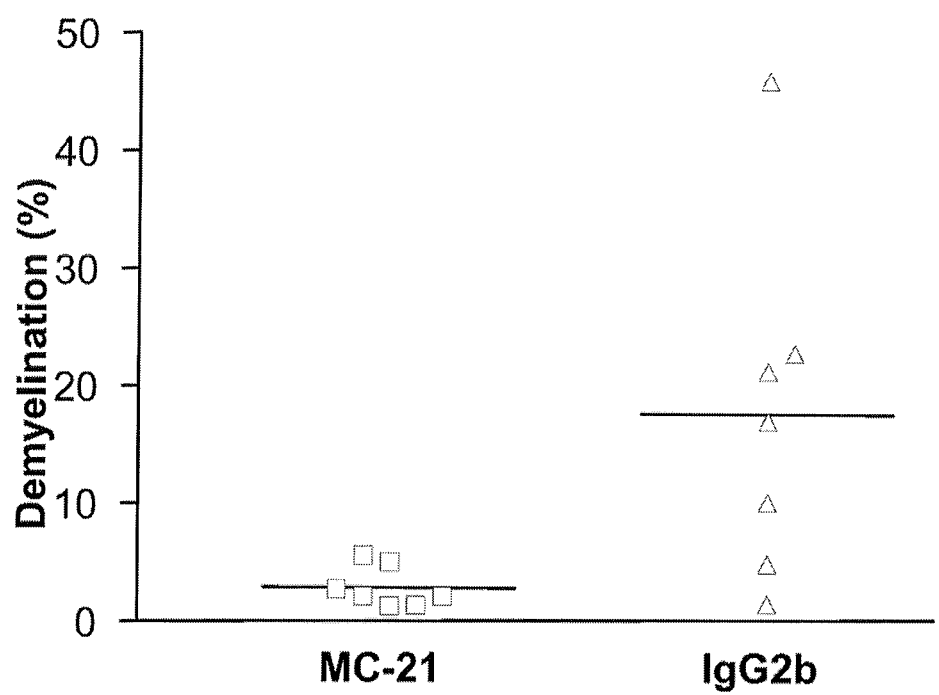
Figure 6:
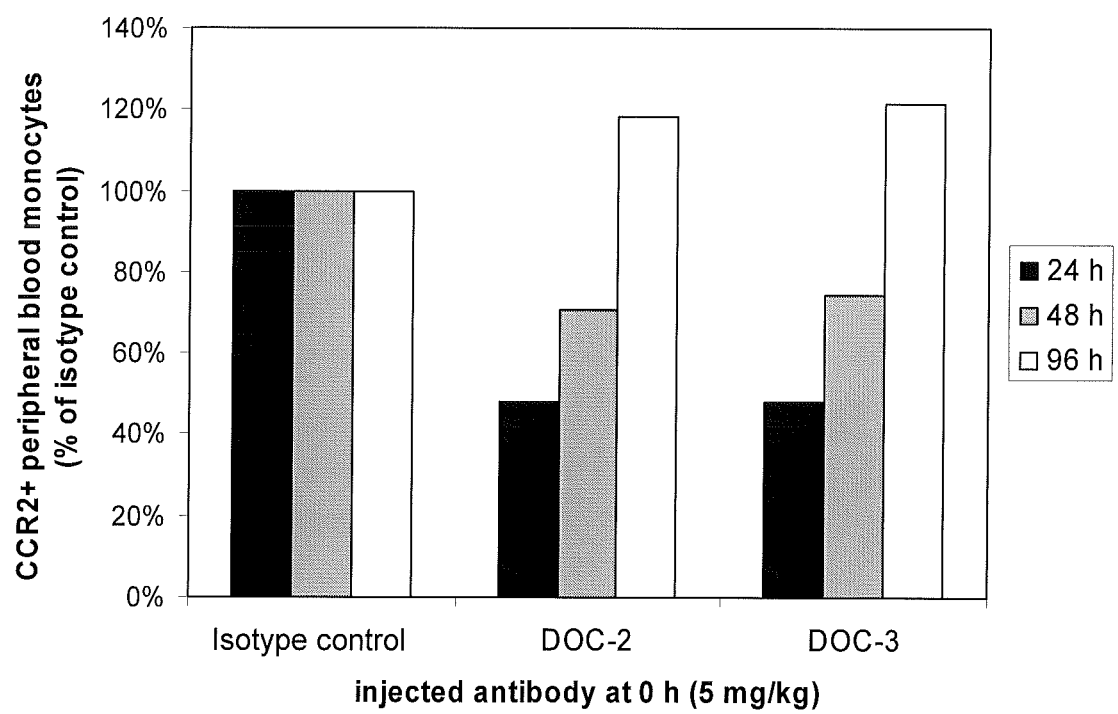

20 µg of the monoclonal anti-CCR2 antibody MC-21 or the respective isotype control (IgG2b) were daily (administered) intraperitoneally from day 17 (peak of the disease) until day 34 after primary immunization, thus beginning from the peak of the disease (EAE score at 2.5, i.e. hind leg weakness with unilateral leg paralysis). A clear and statistically significant reduction of the course of the disease could be observed (FIG. 4). A clinical degree of severity of 1.0 means a tail paralysis. Interestingly, as opposed to the arthritis model, also a relatively high dosage of the MC-21 Ab (250 µg) resulted in an improvement of the clinical course. A functionally relevant activation of basophils in the EAE model by MC-21 could neither be detected by an increase of IL-6 in the serum of treated animals nor by a modulation of the course of the disease via administration of anti-IgE.

The very clear and statistically significant improvement of the clinical severity was accompanied by a clear decrease of the infiltrating mononuclear cells in the central nervous system, as could be shown by the example of the decreased number of $CD3^+$ T cells and $MAC-3^+$ macrophages in MC-21-treated animals at day 35 after the immunization.

Likewise, the tissue damage in the treated animals was clearly reduced. For example, the degree of the demyelination in MC-21-treated animals was, thus, clearly less pronounced than in the isotype control group.

In order to determine which cytokines and chemokines are formed locally in the CNS in animals which are treated with MC-21 and are, therefore, monocyte-depleted, a quantitative PCR was carried out. The bone marrow of the treated animals was removed at day 35 after the immunization, the RNA was extracted, reverse-transcribed and quantified by means of the quantitative real-time (RT) PCR. A clearly lower production of chemoattractant and toxic proteins such as IP-10, MCP-1 and MIP-1a was found in the CNS of MC-21-treated animals.

In a next step, it was examined whether primates (common marmosets, *Callithrix jacchus*) exhibit a cross-reaction with antibodies against human CCR2. In doing so, we have analyzed antibodies DOC-1, DOC-2 and DOC-3, which were produced in the context of the invention, as antibodies against human CCR2.

For the production of the DOC-antibodies, BALB/c-mice that were at least 6 weeks old, were immunized intraperitoneally 6-8 times in intervals of at least 3 weeks with at least 10 million CHO cells stably transfected with full-length CCR2b. Four days after the last immunization the spleen cells were fused with X63.Ag8.653 myeloma cells and cultivated in selective medium. The supernatant of the thus generated hybridomas was tested by means of FACS analysis for the binding to CCR2b-transfected or, as a control, for the binding to CXCR4-transfected CHO cells, respectively. After positive cultures were recloned twice, several monoclonal antibodies (DOC-1, DOC-2 and DOC-3) were obtained which specifically bind to human CCR2 and neither show a cross-reaction with murine CCR2 or CCR5 nor with human CCR1, CCR3, CCR5 or CXCR4. In human peripheral blood, the DOC antibodies bound to a sub-population of the T cells (about 20-30%), as well as to the predominant number of the CD14+ monocytes (>95%). By pre-incubation of the human cells with MCP-1 (1 µg/ml) for 30 min at 37° C., the binding of the CCR2 antibodies to the leukocyte sub-populations described above could virtually completely be inhibited, which can be explained by a MCP-1-induced internalization of CCR2. This additionally showed the specificity of the DOC antibodies.

The DOC antibodies were comprehensively characterized as to their functional features. A summary is presented in the following:

Doc1:
has the isotype IgG3;
binds to loops 1, 2 and 3 of the extracellular CCR2 domains;
does not induce a CCR2 down-modulation on human monocytes from peripheral blood (PBMC) at 37° C.;
blocks the MCP-1-induced CCR2 down-modulation on human PBMC;
blocks the MCP-1- and MCP-3-induced chemotaxis of Monomac6 cells and human PBMC;
shows the partial inhibition of the MCP-1 binding and the MCP-1-induced calcium influx.

Doc2:
has the isotype IgG1;
binds to loop1+first half of loop2 of the extracellular CCR2 domains;
induces a strong CCR2 down-modulation on human PBMC at 37° C. in a concentration-dependent manner;
blocks the MCP-1- and MCP-3-induced chemotaxis of Monomac6 cells and human PBMC;
shows a very effective inhibition of the MCP-1 binding and the MCP-1-induced calcium influx.

Doc3:
has the isotype IgG1;
binds to loop1+second half of loop2 of the extracellular CCR2 domains;
induces a weak CCR2 down-modulation on human PBMC in a concentration-dependent manner;
blocks the MCP-1- and MCP-3-induced chemotaxis of Monomac6 cells and human PBMC;
shows a very effective inhibition of the MCP-1 binding and the MCP-1-induced calcium influx.

In this context, the chemotaxis was measured by means of Transwell filter inserts (pore size 3 μm for PBMC and 5 μm pore size for Monomac6), wherein the cells (PBMC and Monomac6, respectively) were put in the upper well and the chemokines (20-200 ng/ml) were put in the lower well. After incubation for about 60 min, the number of cells migrated into the lower well was measured.

In this context, the calcium influx was measured by means of an assay based on aequorin and luminescence (see Blanpain et al, Molecular Biology of the Cell, vol. 13, 723-737, 2002). The binding of the DOC antibodies to CCR2 was measured by means of flow cytometry, wherein a dye-labeled rabbit anti-mouse Ig antibody was used as a secondary antibody.

For the determination of the binding epitopes of the antibodies, the binding to cells expressing chimeric receptors consisting of CCR2 and CCR5 was determined. The internalization (down-modulation) of CCR2 was also measured by means of flow cytometry.

The cross-reaction of the antibodies DOC-1, DOC-2 and DOC-3 with CCR2 on leukocytes of common marmosets (*Callithrix jacchus*) was examined by means of FACS analysis. For that, whole-blood of common marmosets was incubated with 5 μg/ml of the CCR2 antibody or with the same concentration of isotype control antibodies (IgG1 and IgG3, respectively), which was followed by a PE (phycoerythrin)-labeled secondary antibody (Rabbit (F(ab)2 fragment anti-mouse Ig, R0439, DakoCytomation). After lysis of the erythrocytes, the FACS analysis was carried out. In order to additionally prove the specificity of binding of the DOC antibodies to common marmoset CCR2, for a part of the whole blood, an internalization of CCR2 was induced with human MCP-1 before the incubation with the DOC antibodies. For this, the whole blood was pre-incubated with 1 μg/ml MCP-1 for 30 min at 37° C. and was subsequently examined for the binding of the DOC antibodies as described above. The strong binding of the antibodies DOC-2 and DOC-3 and a slightly weaker binding of the antibody DOC-1 was shown on the monocyte population which is to be delineated in the forward-sideward scatter of the FACS dot plot. About 50% of the thus delineated monocytes bound to DOC-2, DOC-3 and DOC-1. This binding was completely lost when MCP-1-pre-incubated leukocytes were used. The isotype control antibodies did not show any binding to monocytes. Apart from the monocyte sub-population, a binding of the DOC antibodies only occurred to a very small further leukocyte sub-population, which is to be classified as basophilic granulocytes due to its forward-sideward scatter. The monocyte population recognized by the DOC antibodies homogenously was CD11b positive, which was shown by staining with the antibody clone (M1/70, rat anti-mouse CD11b). This CD11b antibody showed a cross-reaction with human and also with common marmoset CD11b.

In addition, the pharmacokinetic features of the DOC antibodies were examined. 24, 48 and 96 hours after injection of the antibodies DOC-2 and DOC-3 (5 mg/kg body weight), the plasma concentrations of the antibodies were measured. For this, plasma of the monkeys was incubated in various dilutions with hCCR2b-transfected CHO cells, and the plasma concentration of the DOC antibody was calculated by means of a standard curve consisting of different dilutions of the antibodies DOC-2 and DOC-3:

| | Plasma concentration (μg/ml) | | |
| --- | --- | --- | --- |
| | 24 h after injection | 48 h after injection | 96 h after injection |
| DOC-2 | 159 | 85 | 3.3 |
| DOC-3 | 20 | 6.3 | 0.9 |

Figure 7:
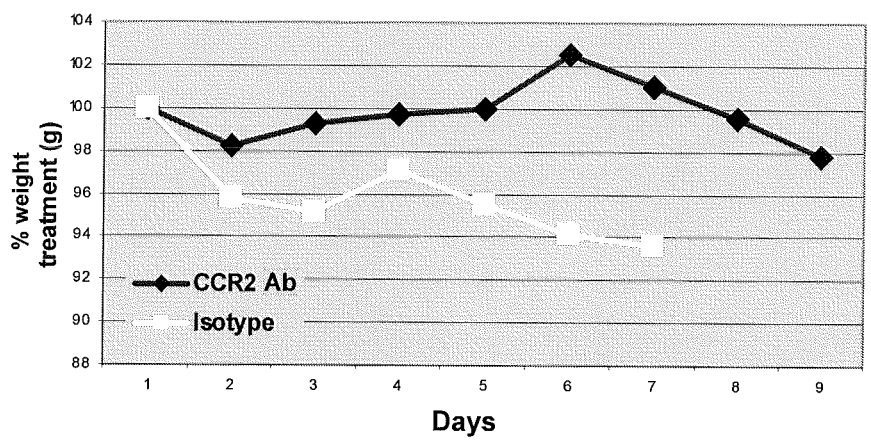
Figure 7:
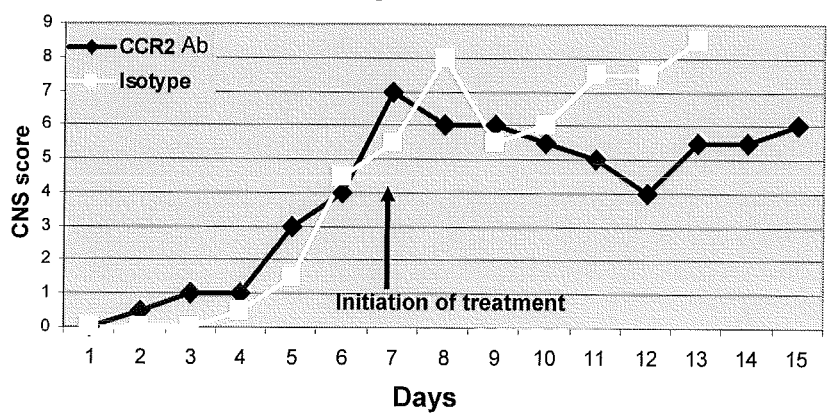
Figure 8:
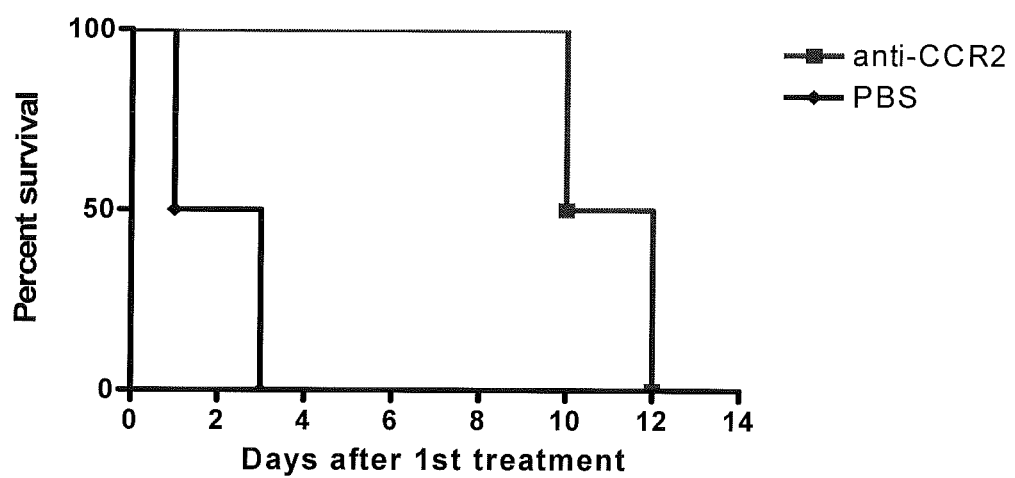

Moreover, it was examined whether a depletion of the CCR2-positive monocytes occurred after injection of DOC-2 or DOC-3 antibodies, respectively. For that, blood was taken 24 hours, 48 hours and 96 hours after injection of the antibodies DOC-2 and DOC-3 and an isotype control antibody, respectively (5 mg/kg body weight each, 2 monkeys per group) and the proportion of CCR2-positive monocytes of the total number of leukocytes was determined by means of FACS analysis. For this purpose, whole-blood was stained with the antibodies DOC-2 or DOC-3, respectively, followed by a phycoerythrin-labeled secondary antibody as described above, and the CCR2-positive monocytes were identified in connection with the forward-sideward scatter. FIG. 7 shows that the proportion of the CCR2-positive monocytes of the total number of leukocytes, on the first day after injection, was reduced in the animals treated with DOC-2 or DOC-3 (to about 50%). The proportion of the CCR2-positive monocytes of the total number of leukocytes in the group treated with isotype control antibodies at the respective days was set to be 100%.

After the efficiency of the anti-human DOC-2 antibody could be shown with a high degree of depletion of inflammatory monocytes in the peripheral blood of common marmosets, we wanted to examine the efficacy of this depleting Ab in the EAE disease model in primates. For this purpose, adult (about 3 years old) female common marmosets (*Callithrix jacchus*) were immunized with the recombinant rat MOG protein in complete Freund's adjuvant (CFA) (50 μg MOG in 600 μl CFA). After 3-4 weeks, the animals started to show first neurological symptoms and inappetence. With the first unambiguous neurological symptoms of disease, we began the therapeutic application with the anti-human CCR2 antibody DOC-2 or the corresponding isotype control (IgG1). Subsequently, the common marmosets were treated every two days with DOC-2 Ab or isotype Ab (5 mg/kg i.p.). During therapy, the primates treated with the DOC-2 Ab, as opposed to the control, showed a stabilization of the weight as well as a decrease of the neurological deficits. In a further experiment, in which we began with the application of the antibodies at the peak of the disease, we could demonstrate a significantly longer time of survival for the lethally progressing EAE as opposed to the control animals.

In summary, the data established in the context of the invention show for the first time that an antibody which depleted CCR2+, GR1+ inflammatory monocytes in vivo, exhibited a clear therapeutic effect both in the mouse model and primate model of MS and in the mouse model of arthritis.

FACS analysis: Whole-blood or splenocytes, respectively, anti-coagulated with EDTA, were incubated for 45 min on ice with directly labeled or unlabeled antibodies, and subsequently removed by three washes. As directly labeled antibodies (labeled with the dyes FITC, PE, PE-Cy5, APC) against murine cells were used: antibodies against CD11b, GR1, CD4, CD19, CD45, DX5, IgE (all from BD-Pharmingen). Monocytes were identified on the basis of their forward and sideward light scatter and on the basis of their expression of CD11b, and were classified depending on expression of Gr1 as Gr1+ and GR1 monocytes.

As not directly labeled antibody were used the CCR2 antibody MC-21 (5 μg/ml) or a rat-IgG2b-isotype control antibody (5 μg/ml, BD-Pharmingen), respectively, followed by biotinylated mouse anti-rat IgG2b (5 μg/ml, BD-Pharmingen), followed by 10% rat serum, followed by streptavidin-PE or streptavidin-PE-Cy5 (DakoCytomation), respectively, and, if appropriate, further directly labeled antibodies. The unlabeled antibodies DOC-1, DOC-2 and DOC-3 or the respective isotype controls (Sigma-Aldrich) were followed by a PE-labeled polyclonal rabbit anti-mouse F(ab)2 fragment (DakoCytomation, R0439).

After staining, the lysis of erythrocytes was carried out by means of FACS lysing solution (BD-Pharmingen). The FACS analysis was performed on a FacsCalibur device of BD-Pharmingen.

ELISA: The measurement of IL-6 in the supernatant of the culture or the EDTA plasma, respectively, was performed with a commercial ELISA (OptEIA) from BD-Pharmingen.

Cell isolation/cell depletion: Naïve basophils were isolated by enrichment of DX-5-positive cells from spleen and bone marrow of mice by means of DX-5-magnetic beads (Miltenyi, isolation according to the manual). Subsequently, a staining with DX-5-APC and CD45-FITC was carried out, by means of which the basophilic granulocytes (DX5+, CD45 low) were isolated by means of FACS-Sort (BD, FACS ARIA). The purity of the thus obtained basophilic granulocytes was more than 95%.

For the depletion of basophilic granulocytes, the starting cells were incubated with anti-IgE FITC antibodies, were washed and subsequently incubated with anti-FITC beads and depleted via magnetic sorting (Miltenyi). The depletion was above 95%.

Collagen-induced arthritis: Male DBA/1-mice, which were at least 8 weeks old, were immunized subcutaneously at the tail base on day 1 with 100 μg bovine collagen (Sigma, C1188) in complete Freund's adjuvant and on day 21 with 100 μg collagen in incomplete Freund's adjuvant. The clinical arthritis score was determined by collecting a score for each paw, which is added for all 4 paws: score per paw: 1 upon swelling of a joint, 2 upon swelling of at least 2 joints, 3 upon swelling of the whole paw, 4 upon deformation of the paw. The treatment with antibodies was carried out as described in the figures.

Experimental autoimmune encephalomyelitis (EAE) in the C57BL/6 mouse: For an active immunization, 6-8 weeks old mice were subcutaneously injected with 200 μg of the $MOG_{35-55}$ peptide, emulsified in CFA (complete Freund's adjuvant) (enriched with 1 mg/ml of *Mycobacterium tuberculosis* (Difco)); followed by 250 ng pertussis toxin, i.v., on the same day and 2 days later. The clinical manifestation of the EAE generally began between the $13^{th}$ and $18^{th}$ day of immunization. The mice were then neurologically evaluated four times a week by the following criteria: 0, no visible neurological symptoms; 0.5, limpness of the distal tail; 1, limpness of the complete tail; 1.5, limpness of the complete tail and weakness of the hind legs; 2, unilateral partial paresis of the hind legs; 2.5, bilateral partial paresis of the hind legs; 3, complete paresis of the hind legs; 3.5, complete paresis of the hind legs and unilateral paresis of the front legs; 4, complete paresis of all four extremities; 5, dead.

For the EAE in common marmosets (*Callithrix jacchus*), recombinant rat-MOG was emulsified in complete Freund's adjuvant (CFA) (50 μg MOG in 600 μl CFA). In portions of 150 μl each, the emulsion was subcutaneously applied at the back at four sites. Two application sites were in the shoulder area and the two others were in the pelvis area. Before application, the corresponding parts of the body were shaved and the skin was disinfected.

Instead of *M. tuberculosis*, we used CFA *Mycobacterium butyricum* at a reduced dose of 1 mg/ml CFA. By this modification, the CFA which normally is strongly effective, was attenuated, yet without losing its effect. This "start-up" immunostimulation was necessary to elicit the autoimmune reaction.

Real-Time PCR (RT-PCR): For this purpose, the animals were sacrificed, the bone marrow was freshly removed and shortly rinsed with sterile PBS. The total RNA was isolated by means of trizol reagent according to the manufacturer's protocol, transcribed into cDNA, and the RT-PCR was carried out.

Histology: The mice were killed via $CO_2$. The spinal column was removed and put into 10% buffered formalin. After the fixation, the bone marrow was removed, embedded and either stained with H&E for the estimation of the leukocyte infiltration or with Luxol fast blue (LFB) for showing the myelinated fibers. Other immunohistochemical stains included various blood cell types (MAC-3 for macrophages: BD Pharmingen; CD3 for T cells: Serotec, Düsseldorf).

The invention claimed is:

1. A medicament containing a monoclonal antibody which specifically binds to loop 1+first half of loop 2 of the extracellular human chemokine receptor CCR2 domain, wherein the monoclonal antibody is Doc-2.

2. A method for depleting monocytes comprising contacting the monocytes with a monoclonal antibody which specifically binds to loop 1+first half of loop 2 of the extracellular human chemokine receptor CCR2 domain, wherein the monoclonal antibody is Doc-2.

3. A method for depleting monocytes in a human subject comprising the step of administering to the subject an effective dose of a monoclonal antibody Doc-2 which specifically binds to loop 1+first half of loop 2 of extracellular human CCR2 domain.

4. The method according to claim 3, wherein the subject has a disease selected from the group consisting of a therapy-refractory multiple sclerosis, a multiple sclerosis in an advanced stage, and a combination thereof.

5. The method according to claim 3, wherein the effective dose does not exceed that dose which is required to achieve a depletion of 95% of the monocytes in the peripheral blood.

6. The method according to claim 5, wherein the effective dose is at least 20% of the monocytes in the peripheral blood are depleted.

7. The method according to claim 3, wherein the effective dose does not cause a more than 20-fold increase of the level of interleukin-6 (IL-6) and/or interleukin-4 (IL-4) in the blood plasma.

8. The method according to claim 3, wherein the effective dose corresponds to 0.01-20 mg of the antibody per kg body weight of the subject per day.

9. A method for depleting monocytes in a human subject comprising the step of administering to the subject a monoclonal antibody which specifically binds to loop 1+first half of loop 2 of the extracellular human CCR2 domain, wherein the monoclonal antibody is Doc-2.

10. The method according to claim 9, wherein the human subject has multiple sclerosis.

11. The method according to claim 3, wherein the antibody is a humanized antibody.

12. The method according to claim 3, wherein the antibody is an antibody of the IgG1 isotype.

13. The method according to claim 9, wherein the antibody is a humanized antibody.

14. The method according to claim 9, wherein the antibody is an antibody of the IgG1 isotype.

15. The method according to claim 3, wherein the effective dose does not exceed that close which is required to achieve a depletion of 90% of the monocytes in the peripheral blood.

16. The method according to claim 3, wherein the effective dose does not exceed that dose which is required to achieve a depletion of 80% of the monocytes in the peripheral blood.

17. The method according to claim 5, wherein the effective dose is at least 30% of the monocytes in the peripheral blood are depleted.

18. The method according to claim 3, wherein the effective dose does not cause a more than 10-fold increase of the level of interleukin-6 (IL-6) and/or interleukin-4 (IL-4) in the blood plasma.

* * * * *